(12) United States Patent
Muslet et al.

(10) Patent No.: US 11,135,335 B2
(45) Date of Patent: Oct. 5, 2021

(54) ELASTOMERIC FILMS HAVING LOW TEAR PROPAGATION

(71) Applicant: CLOPAY PLASTIC PRODUCTS COMPANY, INC., Mason, OH (US)

(72) Inventors: Iyad Muslet, West Chester, OH (US); Jerry Westerkamp, Loveland, OH (US)

(73) Assignee: BERRY FILM PRODUCTS COMPANY, INC., Evansville, IN (US)

( * ) Notice: Subject to any disclaimer, the term of this patent is extended or adjusted under 35 U.S.C. 154(b) by 5 days.

(21) Appl. No.: 15/901,240

(22) Filed: Feb. 21, 2018

(65) Prior Publication Data
US 2018/0264163 A1 Sep. 20, 2018

Related U.S. Application Data

(60) Provisional application No. 62/470,952, filed on Mar. 14, 2017.

(51) Int. Cl.
| | |
|---|---|
| B32B 27/00 | (2006.01) |
| B32B 27/32 | (2006.01) |
| A61L 15/22 | (2006.01) |
| A61F 13/511 | (2006.01) |
| A61F 13/514 | (2006.01) |

(Continued)

(52) U.S. Cl.
CPC ........ A61L 15/225 (2013.01); A61F 13/4902 (2013.01); A61F 13/5116 (2013.01); A61F 13/51121 (2013.01); A61F 13/51401 (2013.01); B32B 7/12 (2013.01); B32B 27/00 (2013.01); B32B 27/08 (2013.01); B32B 27/302 (2013.01); B32B 27/32 (2013.01);
(Continued)

(58) Field of Classification Search
CPC ............ B32B 2250/40; B32B 2250/03; B32B 27/302; C08L 25/06
See application file for complete search history.

(56) References Cited

U.S. PATENT DOCUMENTS 4,663,220 A * 5/1987 Wisneski .................. C08J 5/18
428/221
5,837,352 A 11/1998 English
(Continued)

FOREIGN PATENT DOCUMENTS

| EP | 0691203 A1 | 1/1996 |
| WO | 2007094706 A1 | 8/2007 |

OTHER PUBLICATIONS

Peacock et al. (Polymer Chemistry Properties and Applications, Ch. 18, Polyethylene; Carl Hanser Verlag, Munich: 2006).*
(Continued)

Primary Examiner — Alicia J Sawdon
(74) Attorney, Agent, or Firm — Barnes & Thornburg LLP

(57) ABSTRACT

Multilayer thermoplastic films, and laminates and articles comprising the films, wherein the film comprises at least one inner layer and at least two outer layers, wherein the inner layer comprises a polymeric composition comprising from about 55% to about 95% of one or more non-hydrogenated styrenic block copolymers, olefinic block copolymers, or combinations thereo; and each outer layer comprises at least 20% polypropylene and has a thickness of from about 5% to about 15% of the total film thickness, and further wherein the film has a constant force tear propagation of about 20% or less.

18 Claims, 1 Drawing Sheet

(51) Int. Cl.
*A61F 13/49* (2006.01)
*B32B 27/08* (2006.01)
*B32B 27/30* (2006.01)
*B32B 7/12* (2006.01)

(52) U.S. Cl.
CPC .............. *A61F 2013/51147* (2013.01); *A61F 2013/51409* (2013.01); *B32B 2250/40* (2013.01); *B32B 2307/732* (2013.01)

(56) References Cited

U.S. PATENT DOCUMENTS

| | | | | |
|---|---|---|---|---|
| 5,843,577 | A * | 12/1998 | Ouhadi | C08G 81/028 428/474.7 |
| 6,060,136 | A * | 5/2000 | Patrick | B32B 27/18 426/127 |
| 6,472,084 | B1 * | 10/2002 | Middlesworth | A61F 13/4902 428/156 |
| 7,442,332 | B2 | 10/2008 | Cancio | |
| 9,492,332 | B2 | 11/2016 | Cancio | |
| 2003/0022582 | A1 | 1/2003 | Cree | |
| 2006/0069365 | A1 * | 3/2006 | Sperl | A61F 13/539 604/370 |
| 2006/0115667 | A1 | 6/2006 | Verrocchi | |
| 2006/0216473 | A1 | 9/2006 | Tomany | |
| 2008/0207071 | A1 | 8/2008 | Muslet | |
| 2008/0319130 | A1 * | 12/2008 | Chang | C08L 53/02 525/88 |
| 2009/0088713 | A1 | 4/2009 | Norrby | |
| 2009/0258210 | A1 * | 10/2009 | Iyad | C08L 23/142 428/220 |
| 2011/0282312 | A1 * | 11/2011 | Turner | A61F 13/5148 604/378 |
| 2014/0255658 | A1 | 9/2014 | Muslet | |
| 2016/0016392 | A1 * | 1/2016 | Schuhmann | B32B 7/06 428/36.91 |
| 2016/0200080 | A1 | 7/2016 | Muslet | |

OTHER PUBLICATIONS

International PCT Search Report for PCT/US2018/18935, dated May 7, 2018, CLP-17005 PCT ||, 2 pages.
Chilean Office Action for Chilean Patent App. No. 201902593 dated Jul. 15, 2020, CLP-17003 CL ||, 33 pages.
Chilean Office Action for Chilean Patent App. No. 201902593 dated Jan. 12, 2021, CLP-17003 CL ||, 19 pages.
English Translation of Chilean Office Action and Search Report for Chilean Patent App. No. 201902593 dated Jan. 12, 2021, CLP-17003 CL ||, 14 pages.
Press Release PR Newswire, "Olefinic Block Copolymer (OBC) Market Anticipated to grow at a CAGR of 10% by 2025" Aug. 14, 2018, available at: https://markets.businessinsider.com/news/stocks/olefinic-block-copolymer-obc-market-anticipated-to-grow-at-a-cagr-of-10-by-2025-1027458643.

* cited by examiner

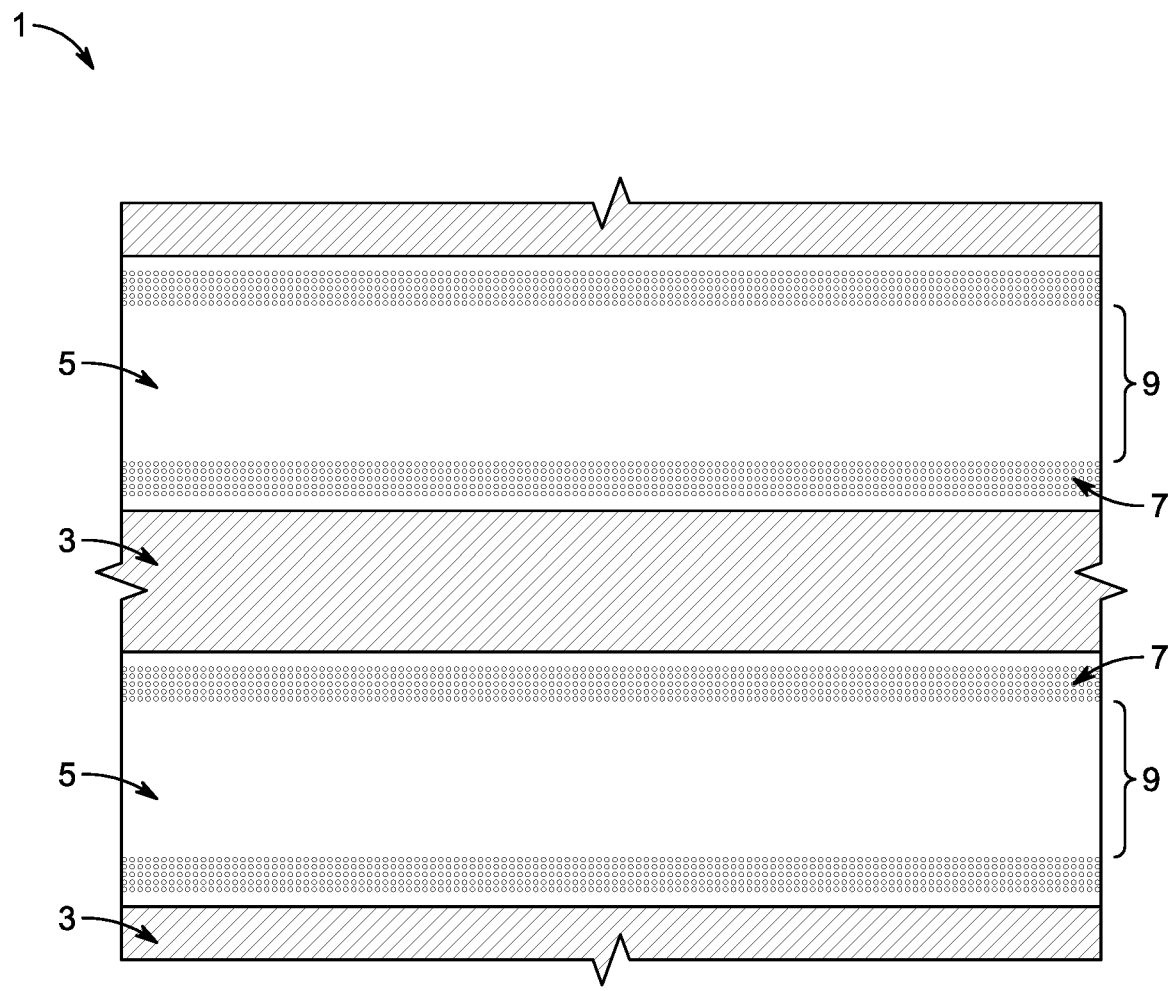

ELASTOMERIC FILMS HAVING LOW TEAR PROPAGATION

RELATED APPLICATIONS

This application claims the benefit of priority of U.S. Provisional Patent Application No. 62/470,952, filed Mar. 14, 2017, incorporated herein by reference in its entirety.

FIELD OF THE INVENTION

The present invention relates to elastomeric thermoplastic films and laminates, which exhibit low tear propagation and are particularly suitable for lamination. The films and laminates are suitable for use in a variety of products, including disposable personal care products.

BACKGROUND OF THE INVENTION

Elastomeric materials are used in disposable absorbent products to provide a snug but comfortable fit that conforms to the body. To ensure a snug fit, it is important that the materials are able to withstand typical conditions that occur while being worn, in particular, being stretched while maintained at or above normal body temperature. If an elastomeric material loses elasticity or integrity, for example by forming holes or becoming delaminated, the material is unsuitable for use in consumer products. In addition, because the elastomeric portion of disposable absorbent products are often in direct contact with the skin, it is important that it has a soft feel, good aesthetic properties, and is breathable.

It has been found that many elastomeric laminates that have acceptable aesthetic properties fail the test for integrity under sustained use. It has further been found that the ultrasonic bonding of laminates presents unique challenges. For example, some films have been found to result in shifting of the web as the web is stretched in the cross-direction during the lamination process. Instead of maintaining a straight path through the laminating apparatus, the web fails to fully engage certain elements, and exhibits back and forth movement in the cross-direction. This can result in processing difficulties, and difficulties in winding the laminates. A need exists, therefore, for elastomeric films and laminates that retain integrity under normal use, are suitable for use in consumer products, and that exhibit good processing characteristics.

SUMMARY OF THE INVENTION

The present invention meets the aforementioned needs by providing elastomeric films and laminates comprising the films which exhibit sufficient strength to withstand the forces typically encountered in regular use of absorbent articles, and yet which are exceptionally soft to the touch. It has been found that both careful control of the processing conditions in combination with a suitable film formulation of both the outer skin and inner core layers are necessary to make laminates that meet customer requirements. In particular, it has been found that the composition and relative thickness of the outer skin layers impact the physical properties of the films, including processibility. It has further been found that by employing a specific pattern of strategically placed ultrasonic bonding, laminates may be made that have excellent strength, haptic, and aesthetic properties.

In one aspect, the present invention provides multilayer thermoplastic films comprising at least one inner layer and at least two outer layers, wherein the inner layer comprises a polymeric composition comprising from about 55% to about 95% of one or more non-hydrogenated styrenic block copolymers, olefinic block copolymers, or combinations thereof; and each outer layer comprises at least 20% polypropylene and has a thickness of from about 5% to about 15% of the total film thickness, and further wherein the film has a constant force tear propagation of about 20% or less.

In another aspect, the present invention provides laminates comprising the aforementioned films.

In another aspect, the present invention provides for articles, including absorbent articles, comprising the aforementioned films.

In another aspect, the present invention provides for a laminate comprising a substrate and a film, wherein the film comprises at least one inner layer and at least two outer layers, wherein the inner layer comprises a polymeric composition comprising from about 55% to about 95% of one or more non-hydrogenated styrenic block copolymers, olefinic block copolymers, or combinations thereof; and each outer layer comprises at least 20% polypropylene and has a thickness of from about 5% to about 10% of the total film thickness, and further wherein the film has a constant force tear propagation of about 20% or less, and further wherein the laminate is made by a process comprising the step of bonding the film to the laminate by means of ultrasonic bonding, thermal point bonding, or combinations thereof.

In another aspect, the film of the aforementioned laminate is pre-activated in the machine-direction, the cross-direction, or both, prior to lamination.

In another aspect, the film of the aforementioned laminate is stretched in the cross-direction and/or the machine-direction by means of diverging disks.

In another aspect, the aforementioned laminate is substantially free of lateral shifting.

In another aspect, the laminates made by the aforementioned process are pre-activated in the machine-direction, the cross-direction, or both, prior to lamination.

BRIEF DESCRIPTION OF THE DRAWINGS

FIG. 1 is a photograph of one non-limiting embodiment of an ultrasonically bonded laminate of the present invention.

DETAILED DESCRIPTION OF THE INVENTION

"Coextruded," "coextrusion," or variants thereof mean a process of making multilayer polymer films wherein each polymer or polymer blend comprising a layer of the film is melted individually. The molten polymers may be layered inside the extrusion die, and the layers of molten polymer films are extruded from the die essentially simultaneously. Coextruded films have no adhesive between the individual coextruded layers.

"Elastomeric," "elastomer," "elastic," or variants thereof mean a film, a laminate, a polymeric composition or material used in a film layer, such that when the film or laminate comprising the material is stretched beyond the original length, recovers to no more than about 1.2 times the original length in the direction of the applied stretching force.

"Permanent set" is the permanent deformation of a material after removal of an applied load. In the case of elastomeric films, permanent set is the increase in length of a sample of a film after the film has been stretched to a given length and then allowed to relax as described herein. Permanent set is typically expressed as a percent increase relative to the original size, therefore, a film that recovers to a length of 1.2 times the original length is said to have a permanent set of about 20%.

"Polyethylene rich," or alternatively, "polyethylene-based," means a polymeric composition comprising at least about 60% by weight of polyethylene monomers. "Polyethylene rich" or "polyethylene-based" is not understood to include polymers comprising mixtures of ethylene and propylene monomers, such as poly(ethylene-propylene).

"Polypropylene rich," or alternatively, "polypropylene-based," means a polymeric composition comprising at least about 60% by weight of polypropylene monomers. "Polypropylene rich" or "polypropylene-based" is not understood to include polymers comprising mixtures of ethylene and propylene monomers, such as poly(ethylene-propylene).

"Gsm" means grams per square meter, and is a measure of the basis weight, which is an industry standard term that quantifies the thickness or unit mass of a film or laminate product.

"Pre-activation," or "activation," or any variants thereof, mean a process by which the elastomeric film or material is rendered more easily stretchable, for example by stretching and allowing a film to relax prior to lamination.

"Substantially free of lateral shifting," as used herein, means that during processing of a film or laminate on a production line, the film or laminate does not exhibit visible lateral movement in the cross-direction plane. Lateral shifting is understood not to include back-and-forth movement of the film or laminate as it is wound for storage.

The films of the present invention are elastomeric films comprising one or more styrenic block copolymers. The films further may comprise polystyrene. When subjected to testing by the constant force tear propagation test, the films, and laminates comprising the films, exhibit a tear propagation of 20% or less. This indicates that the films and laminates meet at least one requirement for use in consumer products, in particular, in elastic portions of disposable absorbent articles.

The films are coextruded multilayer films and may have a structure in which relatively elastomeric layers (B) are alternated with relatively inelastic layers (A). In one particular embodiment, the films have a structure denoted by ABA, wherein A is the outer, or skin, layer and B is the inner, or core, layer. However, variations in the number and arrangement of the layers would be readily apparent to one of skill in the art.

The core layer (or layers in a film having more than three layers) may comprise one or more styrenic block copolymers (SBCs) and/or olefinic block copolymers (OBCs), including styrene-butadiene-styrene (SBS), styrene-isoprene-styrene (SIS), styrene-isoprene-butylene-dtyrene (SIBS), styrene-ethylene-butylene-styrene (SEBS), styrene-ethylene-propylene (SEP), styrene-ethylene-propylene-styrene (SEPS), or styrene-ethylene-ethylene-propylene-styrene (SEEPS) block copolymer elastomers, and copolymers and mixtures of any of the foregoing. Although any SBC may be used, particularly useful SBCs in the films of the present invention are non-hydrogenated SBCs, including but not limited to SBS, SIS and SIBS. Non-limiting examples of SBCs suitable for use in the present invention include those available from Dexco Polymers, Plaquemine, Louisiana, for example, VECTOR® 4111A and 7620.

Olefinic block copolymers suitable for use in the core layer include polypropylene-based (also termed "polypropylene-rich") olefinic block copolymers such as those sold under the trade name INFUSE®, including INFUSE 9507 and 9100, by The Dow Chemical Company of Midland, Mich., and the trade names VISTAMAXX® and IMPACT®, for example VISTAMAXX 6102, available from ExxonMobil Chemical Company of Houston, Tex.

The total amount of SBCs in the core layer may be at least about 50%, from about 50% to about 99%, from about 60% to about 99%, from about 50% to about 95%, from about 55% to about 95%, from about 60% to about 95%, from about 65% to about 95%, from about 70% to about 95%, from about 75% to about 95%, from about 80% to about 95%, from about 70% to about 90%, or alternatively from about 80% to about 90%.

The core layer further may comprise polystyrene in an amount of about 30% or less, and alternatively 25% or less, 20% or less, or from about 1% to about 30%, from about 5% to about 25%, or from about 5% to about 20%. One example of polystyrene suitable for use in the present invention is STYROLUTION 3190, available from PolyOne Corporation, Avon Lake, Ohio.

The films further may comprise other elastomeric polymers, such as elastomeric olefinic random copolymers, polyurethanes, rubbers, vinyl arylenes and conjugated dienes, polyesters, polyamides, polyethers, polyisoprenes, polyneoprenes, copolymers of any of the above, and mixtures thereof.

The outer layers (the A-layers, or skin layers) each may comprise polypropylene in an amount of at least 10%, at least 15%, at least 20%, at least 25%, from about 1% to about 90%, from about 1% to about 85%, from about 1% to about 80%, or from about 1% to about 75%. In one embodiment, the polypropylene is present in an amount of at least 20%, and in another embodiment is present in an amount of from about 20% to about 85%.

Each outer layer further may comprise about 2.5%, 5%, 7.5%, 10%, 15% or 20% of the total film thickness. In some embodiments, the outer layers further each may have a thickness of from about 1% to about 20%, from 3% to about 15%, or from about 5% to about 15% of the total thickness of the film. Alternatively, the outer layers each may have a thickness of from about 1 micron to about 20 microns, or from about 1 microns to about 15 microns, from 1 micron to about 10 microns, from about 1 microns to about 7 microns, and alternatively from about 1 microns to about 5 microns. By way of illustration only, if the total thickness of the film is 100 microns and each outer layer has a thickness of 5 microns, then the outer layers comprise a total of 10% of the film thickness.

The polypropylene in the outer layers may comprise polypropylene, homopolymer polypropylene, impact copolymer polypropylene, as well as other types of polypropylene that would be apparent to one of skill in the art.

The films further may comprise a filler suitable to induce pore formation upon stretching, including but not limited to calcium carbonate. In one embodiment, the filler is present in an amount of from about 30% to about 70%. Additionally or alternatively, the filler may comprise from about 1% to about 25% of an IR-emitting material, non-limiting examples of which include charcoal, bamboo charcoal, nepheline syenite, tourmaline, or combinations thereof.

The films may include master batch and optional components or fillers, such as opacifiers, plasticizers, compatibilizers, draw down polymers, processing aids, anti-blocking agents, viscosity-reducing polymers, and the like. Examples of suitable processing aids and master batch include Ampacet 102795, 100458, and 111040, available from Ampacet Corporation.

The films may have a basis weight of from about 5 gsm to about 100 gsm, from about 15 to about 65 gsm, from 15 to 55 gsm, from 20 to 55 gsm, from 25 to 55 gsm, from 30 to 55 gsm, from 35 to 55 gsm, from 20 to 50 gsm, from 25 to 45, from about 25 gsm to about 35 gsm, of less than about 65 gsm, less than about 60 gsm, less than about 55 gsm, less than about 50 gsm, less than about 45 gsm, less than about 40 gsm, less than about 35 gsm, less than about 30 gsm, less than about 25 gsm, or less than about 20 gsm.

The films have desirable physical properties, including constant tear force propagation, permanent set, cross-direction (CD) load at 100% strain, and machine-direction (MD) load at 10% strain. The percent strain indicates how much the film is stretched, for example, "100% strain means that the film is stretched to twice its original length in the cross direction, and "10% strain" means the film was stretched to 1.1 times its original length in the machine direction. Constant tear force propagation is described below, and to be considered "passing" has a value of 10% or less. The permanent set may be less than 10%, less than 9%, less than 8%, less than 7%, less than 6%, or less than 5%. The machine-direction load at 10% strain may be at least 3 N/cm, at least 3.5 N/cm, and alternatively at least 4.0 N/cm.

The present invention further includes laminates comprising the films described herein. The laminates comprise a substrate attached to one or both surfaces of the film, and may include laminates comprising more than one film and more than two nonwovens.

The substrate may be attached to the film by a variety of means such as adhesive lamination, ultrasonic bonding, extrusion bonding, or other means that would be known to one of skill in the art. In one embodiment, the laminate is ultrasonically bonded, with the resulting laminates comprising ultrasonic welds, or bonds.

The substrate may be any woven or nonwoven material suitable for use with thermoplastic films, and in one embodiment is a spunbond nonwoven. In an alternative embodiment, the substrate is a spunlace nonwoven. The substrate may have a basis weight of about 100 gsm or less, alternatively about 50 gsm or less, alternatively about 25 gsm or less, alternatively about 15 gsm or less, and alternatively from about 1 gsm to about 25 gsm.

The present invention further includes ultrasonically bonded laminates comprising ultrasonically-bonded sites and having a soft feel and appearance, and which pass the constant force tear propagation test. The laminates further exhibit little or no delamination when subjected to the tear propagation test. The laminates comprise a film and at least one substrate, such as a nonwoven, as described herein.

FIG. 1 is a photograph of one non-limiting embodiment of the ultrasonically bonded laminates (1) of the present invention, comprising areas in which the nonwoven (3) extends beyond the film (5). The laminate comprises a plurality of ultrasonically bonded ("UB") zones (7) and non-ultrasonically bonded ("NB") zones (9). In one embodiment, adhesive may be applied to the NB zone and/or the UB zone. In one embodiment, adhesive is applied only to the NB zone.

The ultrasonically bonded area may encompass substantially the entire laminate or a portion thereof. When the ultrasonically bonded area comprises a portion of the laminate, the laminate may comprise one or more UB zones and NB zones. The UB zone may bond one or both edges of the film, as shown in FIG. 1.

The UB zone may extend beyond the edge of the film to encompass nonwoven only, or may include only the area of the film; however, in either case, the UB zone encompasses from about 2% to about 8% of the width of the film. In one particular embodiment, the UB zone has a width of from about 1 mm to about 5 mm, and alternatively from about 2 mm to about 4 mm, and covers the film only, i.e., in what one of skill in the art refers to as the "tack-down" region 7 (FIG. 1). In another particular embodiment, the UB zone extends beyond the film into the area comprising only nonwoven, and has a width of from about 6 mm to about 10 mm.

In one embodiment, the diameter of the ultrasonic point bonds is less than or equal to 1 mm.

Method

An apparatus suitable for making the films of the present invention is described in, e.g., U.S. Pat. No. 9,492,332 (Cancio et al.) and U.S. Pat. No. 7,442,332 (Cancio et al.). Methods described generally therein also are suitable for producing the films of the present invention, with the exception of differences noted herein which contribute to the unique properties of the presently claimed films.

The webs, or films, of the present invention may be coextruded, and may be cast, blown, or formed by any other method which would result in the films described herein.

The thermoplastic polymeric film formulation may be blended in an extruder, with a screw speed of from about 50 rpm to about 75 rpm. During extrusion, the melt curtain temperature may be from about 400° F. to about 500° F. The exact temperature and screw speed will depend upon the formulation of the polymeric compositions. The web, or "melt curtain," comprising the polymeric composition may be extruded (or coextruded if a multilayer film is being formed) from an extruder across a first gap onto an embossed, or chill, roll to form a film, which may be further advanced to a stretching roller across a second gap. The stretching roller may form a nip with additional roller. The nip pressure may be carefully controlled in the range of from about 0.1 psi to about 100 psi.

The film may be stretched in the cross-direction by using CD (cross-directional) intermeshing, or CDI. The depth of intermeshing may vary from about 0 inches to about 0.250 inches, and in particular embodiments may be 0.120 inches, 0.140 inches, 0.160 inches or 0.180 inches. In one embodiment, machine direction interdigitating rollers are used in place of, or in addition to, cross-direction interdigitating rollers, either before or after the CDI section.

When mixing blends such as SIS and polystyrene, or SBS and polystyrene, the screw should provide good mixing to provide homogenous blend. An example of an appropriate mixing element is a Maddock mixer. The temperature profile is set to have a melting temperature between 380° F. and 420° F. for best mixing results.

The film may move from the CDI section to other components, including but not limited to, a corona treatment section, an annealing section, a second machine-direction orientation (MDO) section, and/or a winder, where it is then ready for its intended use. The films may be activated or unactivated prior to further use, and in one particular embodiment, the films are pre-activated in the CD and/or in the MD prior to use.

The resulting films are particularly suitable for lamination to a nonwoven or other suitable substrate. The films may be laminated by a variety of means, including coextrusion, adhesive, thermal point bonding, ultrasonic bonding, and other means of lamination that would be known to one of skill in the art. One non-limiting example of a useful method of laminating the films is described in U.S. Pat. No. 9,498,491 (Sablone et al.).

The films and/or laminates of the present invention are useful for a variety of purposes, including for example use in articles such as personal hygiene products, such as disposable absorbent products. Non-limiting examples include diapers, training pants, adult incontinence pads and pants, swimwear, sanitary napkins, tampons, pantiliners, and/or as absorbent pads or breathable shields to protect clothing from fluids, such as perspiration in specific areas of the body.

The films and/or laminates are particularly useful as fasteners, waistbands and cuffs of absorbent articles. Accordingly, in one embodiment, the present invention is related to an absorbent article comprising the films and/or laminates described herein. In one embodiment, the absorbent article is a diaper. Other uses include as diaper backsheets or ears (closure tabs), pouches for packaging, wrapping products such as personal hygiene items, as well as foods such as sandwiches, fruits, vegetables and the like, breathable poly bags such as breathable diaper poly bags, building applications, such as roofing and wall linings, and backsheets for flooring and carpeting.

Test Methods

Constant Force Tear Propagation Test

Cut a sample from a film or a laminate having a trapezoidal shape in which the top has a width of 3," the bottom has a width of 2," and the sides a length of 6". Staple the top edge securely to a cardboard backing. Stretch the sample to a length of one and a half times the original length (150% strain) and staple the bottom edge into place. Using a fine blade, cut an approximately 1-2 mm horizontal slit (parallel with the top and bottom edges) in approximately the middle of the sample. Record the initial width of the slit. Place the sample in an oven at 40° C. Record the width of the slit after a period of two hours (final width), and if desired, at regular time intervals up to twelve hours after placing in the oven. A sample is considered to have passed the constant force tear propagation test if, after a period of at least two hours, the final width of the slit has increased by 20% or less than the initial width. In other words, if a slit having a width of 1 mm has increased to no more than 1.2 mm after a period of two hours, the sample is deemed to have passed the test and is described as "having a tear propagation of 20% or less."

Differential scanning calorimetry (DSC) testing is performed according to the method described in ASTM D-3418-12, using the following procedure: 1: Ramp 10.00° C./min to 225.00° C.; 2. Mark end of cycle; 3: Ramp 5.00° C./min to -90.00° C.; 4: Mark end of cycle; 5: Ramp 10.00° C./min to 225.00° C.; 6: Mark end of cycle; 7: End of method. The data represented by "DSC First Melt" in Table 2 represents the integral of substantially all area under the curve after the first cycle (i.e, after step 2 above). The data represented by "DSC Second Melt" in Table 2 represents the integral of substantially all area under the curve after the second cycle (i.e., after step 6 above).

Permanent set is measured by the Two Cycle Hysteresis Test, as described in U.S. Patent Publication 2016/0200080 (Muslet et al.), with the following changes: All specified percent engineering strains are 100% as opposed to 130%. The percent set is defined as the percent engineering strain after the start of the second load cycle (from segment 6) where a force of 10 grams is measured (percent set load=10 grams). The temperature of the room is about 73° F.+/−5° F. (i.e., engineering strain=130%.

"Tensile strength," means the load required to induce a break ("load at break") in the film in either the cross-direction (CD) or the machine-direction (MD). Tensile strength is expressed in units of N/cm or equivalent units thereof, and is determined by ASTM method D822-02, using the following parameters: Sample Direction=MD×CD; Sample size=1 inch width×6 inch length; Test speed=20 in/min; Grip distance=2 inch. Grip size=3 inch wide rubber faced grips evenly gripping sample.

EXAMPLES

Table 1 includes films of the present invention (Examples 1-8) and comparative examples 9-12. The films were coextruded and, with the exception of example 11, have the structure AB/A, wherein A represents the outer, or skin, layers and B represents the inner, or core, layer. In all examples, the remainder of the polymeric composition of the A- or the B-layers is comprised of processing aids and master batch, as would be understood by one of skill in the art.

The films were laminated to a 25 gsm nonwoven (Fitesa) on a FMD-M2-00013 lamination system.

TABLE 1

| Ex. | Film Structure (Relative Layer Thickness as a % of Total Film Thickness) | Thickness A-Layer (microns) | % Polypropyene in A-layer | Polymeric Comp. B-Layer or Monolayer* | Polymeric Composition A Layers* | Basis Wt. (gsm) |
|---|---|---|---|---|---|---|
| 1 | A/B/A (5%/90%/5%) | 1.9-2.9 | 30% | 86% SBS, 10% PS | 47% LLDPE, 30% PP, 14% LDPE | 45 |
| 2 | A/B/A (5%/90%/5%) | 2.5-3.7 | 30% | 86% SBS, 10% PS | 47% LLDPE, 30% PP, 14% LDPE | 45 |
| 3 | A/B/A (5%/90%/5%) | 1.2-2.5 | 30% | 86% SBS, 10% PS | 47% LLDPE, 30% PP, 14% LDPE | 45 |
| 4 | A/B/A (7.5%/85%/7.5%) | 3.0-4.5 | 30% | 86% SBS, 10% PS | 47% LLDPE, 30% PP, 14% LDPE | 45 |
| 5 | A/B/A (10%/80%/10%) | 4.1-6.2 | 30% | 86% SBS, 10% PS | 47% LLDPE, 30% PP, 14% LDPE | 45 |
| 6 | A/B/A (10%/80%/10%) | 3.2-4.9 | 80% | 80% SIS, 15% PS | 80% PP, 10% LLDPE, 10% LDPE | 45 |
| 7 | A/B/A (10%/80%/10%) | 3.2-3.7 | 80% | 57% SIS, 19% SEEPS, 19% Vistamaxx ® | 80% PP, 10% LLDPE, 10% LDPE | 45 |
| 8 | A/B/A | 4.0.-6.5 | 80% | 57% SIS, | 80% PP, | 35 |

TABLE 1-continued

| Ex. | Film Structure (Relative Layer Thickness as a % of Total Film Thickness | Thickness A-Layer (microns) | % Polypropylene in A-layer | Polymeric Comp. B-Layer or Monolayer* | Polymeric Composition A Layers* | Basis Wt. (gsm) |
|---|---|---|---|---|---|---|
| | (10%/80%/10%) | | | 19% SEEPS, 19% Vistamaxx®, 58% Infuse®9100, 36% Infuse®9507 | 10% LLDPE, 10% LDPE | |
| 9 | A/B/A (5%/90%/5%) | 1.7-4.0 | 30% | | 47% LLDPE, 30% PP, 14% LDPE | 35 |
| 10 | A/B/A (5%/90%/5%) | 3.3-4.5 | 0% | SEBS, SIS, percentages unknown | LDPE | 55 |
| 11 | Monolayer | N/A | 0% | 92% Vistamaxx® 6102 | N/A | 25 |
| 12 | A/B/A (5%/90%/5%) | 0.8-1.2 | 0% | 92% Vistamaxx® 6102 | 25% OBC, 75% LLDPE | 25 |

Table 2 includes various physical parameters of the films of the present invention (Examples 1-8) and comparative examples 9-12.

TABLE 2

| Ex. | DSC First Melt (J/g) | DSC Second Melt (J/g) | Perm Set (%) | Constant Tear Force Propagation Test | CD Load at 100% (N/cm) | MD Load at 10% (N/cm) | Observ. During Lamination |
|---|---|---|---|---|---|---|---|
| 1 | 6.74 | 8.80 | 1.2 | Pass | 1.3 | 4.1 | Stable |
| 2 | 10.06 | 10.38 | 1 | Pass | 1.1 | 3.6 | Stable |
| 3 | 6.31 | 9.11 | 1.3 | Pass | 0.83 | 3.8 | Stable |
| 4 | 10.01 | 12.34 | 1.5 | Pass | 0.89 | 4.6 | Stable |
| 5 | 17.28 | 19.34 | 1.4 | Pass | 1 | 5.3 | Stable |
| 6 | 15.79 | 14.30 | 5.7 | Pass | 0.82 | 5.8 | Stable |
| 7 | 18.04 | 16.58 | 6.3 | Pass | 1 | 4.9 | Stable |
| 8 | 18.20 | 17.63 | 3.2 | Pass | 0.8 | 4.3 | Stable |
| 9 | 35.92 | 40.14 | 9.3 | Pass | 1.1 | 2.2 | Web Shift |
| 10 | 19.87 | 26.13 | 3 | Pass | 0.78 | 3.3 | Web Shift |
| 11 | 8.13 | 6.55 | 15 | Fail | N/A | 1.1 | Web Shift |
| 12 | 10.91 | 13.25 | 15 | Fail | N/A | 1 | Web Shift |

As can be seen in the above tables, the films of the present invention both pass the constant force tear propagation test and are stable during lamination, meaning that the web maintains a relatively centered position during processing and winding and is therefore substantially free of lateral shifting. The comparative films, however, fail the constant force tear propagation test and/or exhibit unacceptable lateral shifting of the web, which compromises further processing into an article.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern. All ranges are inclusive and combinable. To the extent a value is not explicitly listed, it is understood to be implied as an option if included in a recited range.

Whereas particular embodiments of the present invention have been illustrated and described, it would be obvious to those skilled in the art that various other changes and modifications can be made without departing from the spirit and scope of the invention. It is therefore intended to cover in the present claims all such changes and modifications that are within the scope of this invention.

What is claimed is:

1. A laminate comprising a substrate and a multilayer thermoplastic film, the multilayer thermoplastic film comprising an inner layer and two outer layers,
    wherein the inner layer comprises a polymeric composition comprising (a) from about 55% to about 95% by weight of one or more non-hydrogenated styrenic block copolymers selected from the group consisting of SBS, SIS, and SIBS, and (b) an olefinic block copolymer;
    and each outer layer comprises polypropylene and polyethylene, the polypropylene being at least 20% by weight and each outer layer has a thickness of from about 5% to about 15% of the total film thickness, and,
    wherein the film has a constant force tear propagation of about 20% or less.

2. The laminate of claim 1, wherein the non-hydrogenated styrenic block copolymers are present in an amount of from about 60% to about 90% by weight.

3. The laminate of claim 1, wherein the thickness of each outer layer of the film is from about 1 micron to about 15 microns.

4. The laminate of claim 1, wherein the film has a basis weight of from about 20 gsm to about 55 gsm.

5. The laminate of claim 1, wherein the has a permanent set of less than about 8%.

6. The laminate of claim 1, wherein the film has a machine-direction load at 10% strain of at least 3.5 N/cm.

7. The laminate of claim 1, wherein the polymeric composition of the film further comprises a polypropylene-rich polymer.

8. The laminate of claim 1, wherein each outer layer comprises from about 10% to about 50% by weight of LLDPE.

9. The laminate of claim 1, wherein each outer layer comprises from about 10% to about 15% by weight of LDPE.

10. The laminate of claim 1, wherein the polypropylene in each outer layer is present in an amount of from about 25% to about 80% by weight.

11. The laminate of claim 1, wherein the laminate comprises bond sites throughout substantially the entire surface of the laminate.

12. The laminate of claim 11, wherein the bond sites are ultrasonically-bonded sites.

13. The laminate of claim 1, wherein the laminate comprises bond sites in at least one ultrasonically-bonded zone.

14. The laminate of claim 13, wherein the width of each ultrasonically-bonded zone is from about 1 mm to about 5 mm.

15. The laminate of claim 13, wherein the total width of the ultrasonically-bonded zones comprises from about 2% to about 8% of the width of the film.

16. The laminate of claim 13, wherein the ultrasonically-bonded zone is in a tack-down region.

17. An absorbent article comprising the laminate of claim 1.

18. The laminate of claim 1, wherein each outer layer of the film comprises (i) 30% to 80% by weight polypropylene, (ii) LDPE, and (iii) LLDPE, and the inner layer comprises from about 60% to about 90% by weight non-hydrogenated styrenic block copolymers.

\* \* \* \* \*